United States Patent [19]

da Encarnação

[11] Patent Number: 5,556,384
[45] Date of Patent: Sep. 17, 1996

[54] SELF-DESTRUCTIVE HYPODERMIC SYRINGE

[76] Inventor: Fernando A. F. da Encarnacão, Rua Leobina Pereira, 38 (J. São Paulo, 50910-260 Recife, Brazil

[21] Appl. No.: 423,553

[22] Filed: Apr. 17, 1995

[30] Foreign Application Priority Data

Jul. 18, 1991 [BR] Brazil ..................................... 9103269

[51] Int. Cl.$^6$ ..................................................... A61M 5/00
[52] U.S. Cl. ......................... 604/110; 604/218; 604/220
[58] Field of Search .................................. 604/110, 220, 604/111, 187, 198, 263, 227, 222, 181, 213, 218

[56] References Cited

U.S. PATENT DOCUMENTS

| | | | |
|---|---|---|---|
| 3,747,812 | 7/1973 | Karman et al. | 604/220 |
| 5,180,369 | 1/1993 | Dysarz | 604/110 |
| 5,263,934 | 11/1994 | Haak | 604/220 |
| 5,290,228 | 3/1994 | Uemura et al. | 604/220 |

FOREIGN PATENT DOCUMENTS 2187961  9/1987  United Kingdom ................ 604/218

*Primary Examiner*—John D. Yasko
*Assistant Examiner*—Ronald K. Stright, Jr.
*Attorney, Agent, or Firm*—Harrison & Egbert

[57] ABSTRACT

The present invention is a self-destructive syringe that includes a cylindrical body with a hypodermic needle at one end, a breakable circle, and a retaining ring. The syringe has a piston with a sharp point at the front of the piston. When the piston reaches the lower end of the stroke, the sharp point on the piston perforates the breakable circle while the edges of the piston are encased in the retaining ring. The retaining ring has cutting edges which will damage the seal of the piston if the piston is returned for reuse. A seal, supported by flanges, is positioned at an opposite end of the syringe so as to prevent the piston from reaching the destructive end of the syringe.

8 Claims, 2 Drawing Sheets

U.S. Patent  Sep. 17, 1996  Sheet 2 of 2  5,556,384
FIG. 3
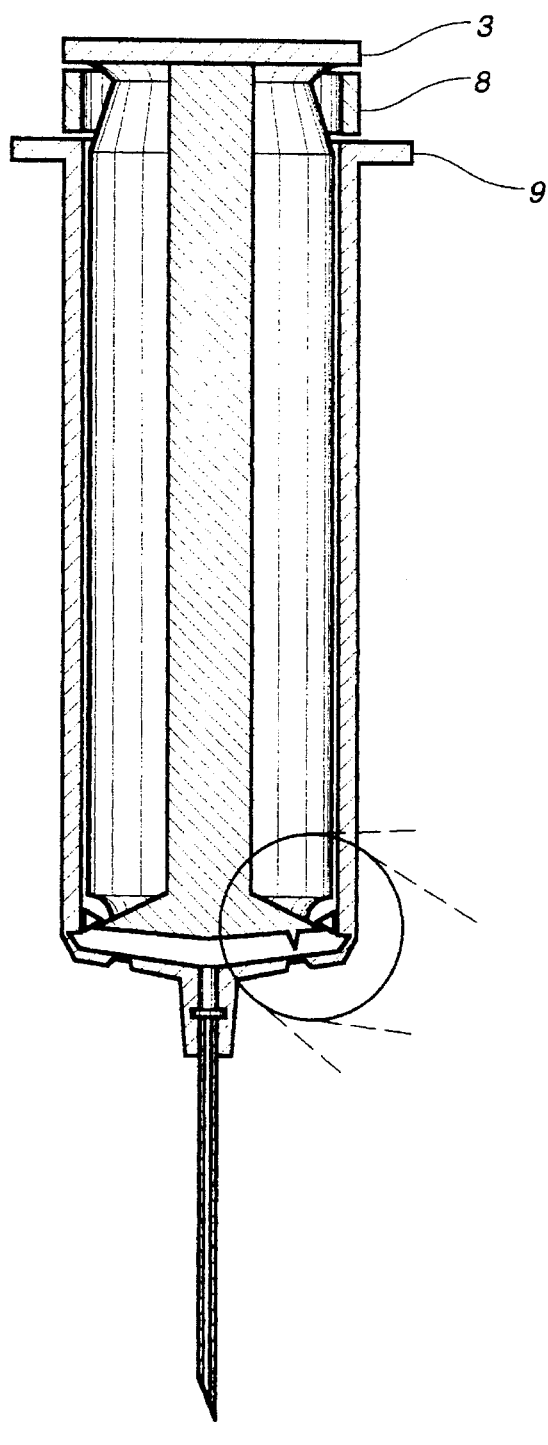
FIG. 4
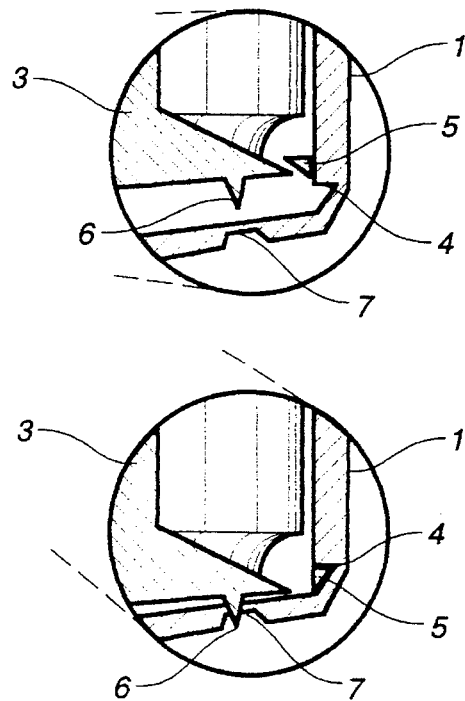
FIG. 5

5,556,384

SELF-DESTRUCTIVE HYPODERMIC SYRINGE

TECHNICAL FIELD

The present invention relates to a self-destructive hypodermic syringe assembly which can perform any and all injection of fluids into or withdraw them from the human body and its cavities, just like a conventional hypodermic syringe.

BACKGROUND ART

So far, two types of hypodermic syringes have been manufactured for many years, both of them reusable. The first ones, made of glass and replaceable hypodermic needles, lasts over a century; in recent years a second type emerged from the medical equipament factories, the ones called discarded type set with a plastic body unit and the standard needle, which both should be discarded after the first and sole use. Irrespective of the material used in this medical equipment, the basic components are identical in form and function. The standard syringe includes a cylindrical body (or capsule) fitted snugly onto a hollow needle, and an air-tight piston that features a wider section of its top part to help operator fingers to push it down inserting the desired liquid into the human body or pulling it back on to collect the proper material.

The thrown-away type hypodermic syringes and hypodermic needles are already sterilized at the factory by state-of-the-art devices, and free from any and all molesting agents, and packed into sealed plastic envelopes to remain aseptic for years until the moment of use. However, this directive became useless due to the fact that non-authorized people and drug addicts kept on using them indiscriminately and this led to a spread of diseases and became a public nuisance.

The reusing of hypodermic syringes and their hypodermic needles are conducive to contamination and in general use among drug addicts and infected patients can and will produce collateral harmful effects in the human body.

The self-destructive hypodermic syringe and its hypodermic needle eliminates, once for all, any reusing of the assembly so providing the safety and reliability demanded by all.

It is an object of the present invention to provide a self-destructive syringe that prevents reuse of the syringe.

It is another object of the present invention to provide a self-destructive syringe that is easy-to-use, reliable, and relatively inexpensive.

It is a further object of the present invention to provide a self-destructive syringe that resists the transmission of disease.

These and other objects and advantages of the present invention will become apparent from a reading of the attached specification and appended claims.

SUMMARY OF THE INVENTION

The present invention is a self-destructive syringe that includes a cylindrical body with a hypodermic needle at one end, a breakable circle, and a retaining ring. The syringe has a piston with a sharp point at the front of the piston. When the piston reaches the lower end of the stroke, the sharp point on th piston perforates the breakable circle while the edges of the piston are encased in the retaining ring. The retaining ring has cutting edges which will damage the seal of the piston if the piston is returned for reuse. A seal, supported by flanges, is positioned at an opposite end of the syringe so as to prevent the piston from reaching the destructive end of the syringe.

BRIEF DESCRIPTION OF THE DRAWINGS

FIG. 3 shows the internal and external features of the assembly as well as the self-destructive components as per the lines A—A of FIG. 2.

FIG. 4 is an isolated view of the circled area of FIG. 3 of the operation of the piston and retaining ring of the present invention prior to use of the syringe.

FIG. 5 is an isolated view of the circled area of FIG. 3 following the use of the syringe.

DETAILED DESCRIPTION OF THE PRESENT INVENTION

Figure 1:
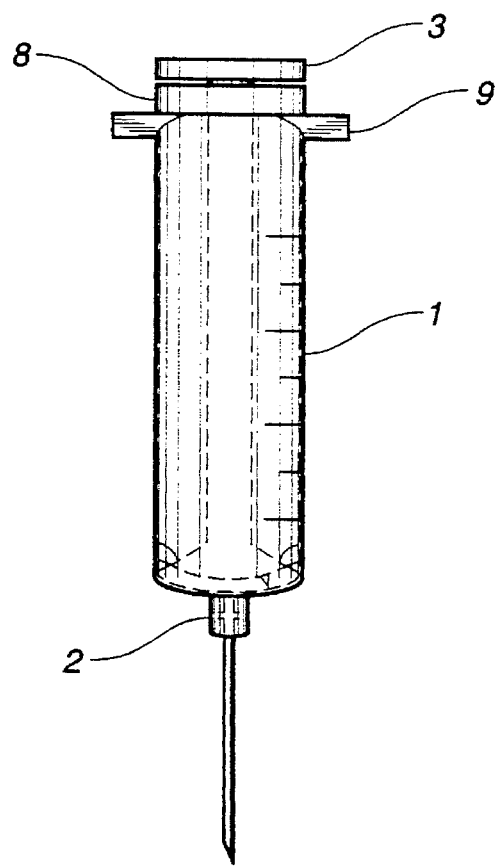
FIG. 1 is a plan view of the self-destructive hypodermic syringe assembly and its built-in device.
Figure 2:
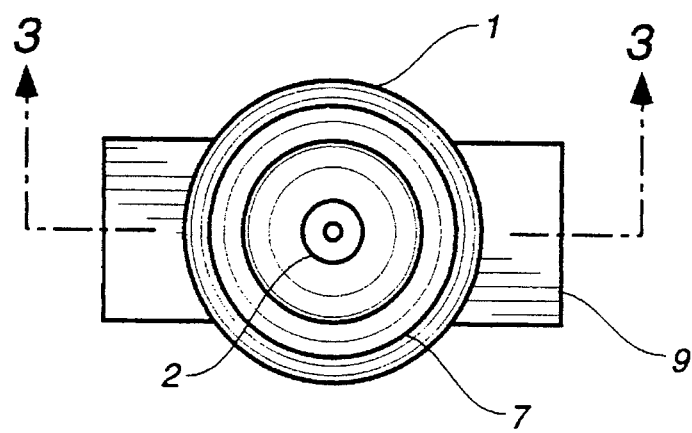
FIG. 2 a end view of the assembly, where the body (1) stands out, the hypodermic needle cast on its frontal basis (2) and the breakable circle (7).

One can infer from the drawings attached that the equipment is composed of a cylindrical body (capsule) (1) in which the hypodermic needle is cast-on to its frontal basis (2) and a breakable circle. Near the frontal basis lower end of the body (1) when it becomes aligned with the piston stroke end travel, the piston (3) faces the retaining ring (4). On the other hand, in the top section of the body (1), a supporting flange (9) and a specially designed safety ring prevents the cutting blade from acting on the breakable circle before the hypodermic syringe is used.

On the interior of the cylindrical body 1, the piston 3 has a sharp point 6 formed on its frontal surface. In a downstroke of the piston 3, the sharp point 6 will perforate the breakable circle so as to make the complete assembly useless.

The lower rims of the piston (3) carry out a steady pressure against the internal walls of the capsule (1) to avoid any seepage to the top section of the piston (3) and at the completion of the piston down stroke, the rims spread out and are encased into the retaining ring (4) while the small sharp point perforates the breakable circle (7).

FIG. 4 shows distinctively the piston rims (3) at the initial stage, to allow the free sliding of the piston (3) to suck or to press the liquid inside the body (1). In this figure one can also see the sharp point (6) on the front part of the piston, to perforate the breakable circle (7) as well as the retaining ring (4) which holds in the piston (3) at the lower limit of its travel and destructs the piston rims (3) if any attempt is made to move it back.

FIG. 5 eminences the piston (3) condition at the lower end of the stroke and also the course and the way the piston rims (3) are curbed by the retaining ring (4) besides the resting position of the sharp point (6) to perforate the breakable circle (7) thus making the unit (1) completely useless.

It is clear that the piston (3) and the body (1) are damaged beyond repair after the first and only use.

The present invention is a hypodermic syringe and hypodermic needle for injection or drain of fluids in the human body, which destroys itself after the first and sole use, not allowing therefore, the condemned reutilization of any of its parts (needle included), considering that—in a hypodermic syringe of this type—the needle is cast to body (1) thus forming a monobloc.

The self-destructive hypodermic syringe is composed of a cylindrical body (1) with a hypodermic needle cast to its frontal basis (2), a breakable circle (7) and a retaining ring (4), formed by the sheathing of the side wall close to the body frontal basis (1) so that when the piston (3) reaches the lower end of its stroke, a small sharp point (6)—located on the frontal part of the piston (3)—perforates the breakable circle (7) (thus making both the body (1) and the needle useless) while the edges (5) of the frontal perimeter of the piston are encased into the retaining ring (4).

Any attempt toward bringing the piston back to the upper part of the body (1) will make the cutting edges of the retaining ring to irreparably damage the sealing parts (5) (air-tightness) of the piston (3) which, in such conditions, lose the capacity to vary the pressure of the internal volume in the body (1). To avoid the self-destruction of the above-described hypodermic syringe before its normal use, a seal (8)—supported by the flanges (9)—is placed on the upper part of the body (1), thus avoiding the piston (3) from reaching its lower end and also impeding the expurgation of the air volume in front of the piston (3) so preventing the use of the hypodermic syringe without breaking the seal.

I claim:

1. A self destructive syringe comprising:

a cylindrical body having a needle at one end;

a breakable ring formed in said end of said cylindrical body adjacent said needle;

a piston slidably received within said cylindrical body, said piston having a sealing member extending circumferentially therearound so as to form an air-tight seal with an inner wall of said cylindrical body, said piston having a frontal portion with a sharp point formed thereon, said sharp point having a sharpness suitable for perforating said breakable ring upon contact with said breakable ring; and a retaining ring means formed in said cylindrical body generally adjacent said end, said retaining ring means for encasing said sealing member of said piston when said sharp point contacts said breakable ring, said retaining ring means having sharp edges so as to damage said sealing member of said piston when said piston is moved from said end of said cylindrical body.

2. The syringe of claim 1, further comprising:

a seal means affixed to an opposite end of said cylindrical body opposite said needle, said seal means for preventing said piston from contacting said breakable ring prior to use.

3. The syringe of claim 2, said seal means being supported by flanges extending from said opposite end of said cylindrical body.

4. The syringe of claim 2, said seal means comprising a breakable seal which is breakable upon an initial use of said syringe.

5. The syringe of claim 1, said sealing member in a constant pressure contact with said inner wall until said sealing member enters said retaining ring means.

6. The syringe of claim 5, said sealing member receivable within said retaining ring means such that said piston cannot move away from said end of said cylindrical body without destroying the air-tight relationship of said sealing member with said inner wall.

7. The syringe of claim 1, said retaining ring means being a generally V-shaped indentation extending around an inner surface of said cylindrical body.

8. The syringe of claim 1, said retaining ring means receiving said sealing member simultaneously with the breaking of said breakable ring by said piston.

\* \* \* \* \*